(12) United States Patent
Ruider et al.

(10) Patent No.: US 6,388,137 B1
(45) Date of Patent: May 14, 2002

(54) METHOD OF PURIFYING TRIETHANOLAMINE

(75) Inventors: Günther Ruider, Wachenheim; Karl-Heinz Ross, Grünstadt, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/857,051

(22) PCT Filed: Nov. 25, 1999

(86) PCT No.: PCT/EP99/09138

§ 371 Date: May 31, 2001

§ 102(e) Date: May 31, 2001

(87) PCT Pub. No.: WO00/32553

PCT Pub. Date: Jun. 8, 2000

(30) Foreign Application Priority Data

Dec. 1, 1998 (DE) .......................... 198 55 383

(51) Int. Cl.⁷ ............... C07C 209/84; C07C 209/86; C07C 213/10
(52) U.S. Cl. ........................ 564/499; 564/475
(58) Field of Search .................... 564/499, 475

(56) References Cited

U.S. PATENT DOCUMENTS

| 3,040,076 A | * | 6/1962 | Seidel et al. ............... 554/142 |
| 3,151,166 A | * | 9/1964 | Milligan ..................... 564/475 |
| 3,207,790 A | | 9/1965 | Glew |
| 3,742,059 A | | 6/1973 | Dowd |
| 3,819,710 A | | 6/1974 | Jordan |
| 4,567,303 A | | 1/1986 | Boettger |
| 4,673,762 A | | 6/1987 | Paslean |
| 5,545,757 A | | 8/1996 | Hammer |

FOREIGN PATENT DOCUMENTS

| DE | 22 25 015 | 12/1972 |
| EP | 004 015 | 9/1979 |
| EP | 036 152 | 9/1981 |
| EP | 673 920 | 9/1995 |
| GB | 760 215 | 8/1951 |
| GB | 1 062 730 | 3/1967 |
| GB | 1092449 | 11/1967 |
| GB | 1 453 762 | 10/1976 |

OTHER PUBLICATIONS

Chem.Abst.vol. 70,1969,77312, 77305f.
Derwent Abst. 63384T,Chem. Abst.vol. 77,1972 4879f.
Derwent Abst.87–047397/07, 1987.
Derwent Abst. 87–067647/10, 1987.
Chem.&Engineering News 1996, 9/16, Seite 42.
Thermal Transformation of Ethanolamines, Smirnova et al., J.of Appl. Chem. of the USSR 61, S. 1508–9 (1989).

* cited by examiner

*Primary Examiner*—Brian J. Davis
(74) *Attorney, Agent, or Firm*—Keil & Weinkauf

(57) ABSTRACT

Method of purifying triethanolamine prepared by reacting aqueous ammonia with ethylene oxide in the liquid phase under pressure and at elevated temperature by removing excess ammonia, water and monoethanolamine from the reaction product, reacting the resulting crude product with ethylene oxide at temperatures of from 110 to 180° C., and then rectifying the mixture in the presence of phosphorous or hypophosphorous acid or compounds thereof.

8 Claims, No Drawings

METHOD OF PURIFYING TRIETHANOLAMINE

This application is a 371 of PCT/EP99/09/38 filed Nov. 25, 1999.

The present invention relates to a method of purifying triethanolamine (TEA) prepared by reacting aqueous ammonia with ethylene oxide in the liquid phase under superatmospheric pressure and at elevated temperature.

Important fields of use of TEA are, for example, soaps, detergents and shampoos in the cosmetics industry or else dispersants and emulsifiers.

For these fields of use, it is desirable for the TEA to be water-clear and colorless and to retain these properties even over prolonged storage times.

It is known that pure TEA obtained by a fractional distillation of a TEA crude product which has been obtained by reacting aqueous ammonia with ethylene oxide and distilling off monoethanolamine (MEA) and diethanolamine (DEA), and initially colorless (color number: about 0 to 20 APHA according to DIN-ISO 6271(=Hazen)), can, after a storage time of from about 4 to 6 weeks, even in a sealed pack and with the exclusion of light, gradually turn pale pink and finally, particularly when left to stand in light, can turn yellow to brown. This effect is accelerated by the action of relatively high temperatures. (See e.g.: G. G. Smirnova et al., J. of Applied Chemistry of the USSR 61, (1988) p. 1508–9, and Chemical & Engineering News 1996, September 16, page 42, middle column).

According to Chemical & Engineering News 1996, September 16, page 42, one mole of TEA decomposes at elevated temperature to give one mole of ethanolamine and two moles of acetaldehyde. Acetaldehyde condenses to give crotonaldehyde which, in turn, forms a Schiff's base with ethanolamine. This unsaturated Schiff's base leads, with 1,4-polymerization, to colored products in the TEA.

As well as the time-consuming storage experiments in which the APHA color number (according to DIN-ISO 6271) of TEA is measured as a function of the storage time, another method which has proven successful for assessing the color quality of pure TEA is the "acid neutralization test".

This "acid neutralization test" permits assessment of the shelf life as regards color of freshly prepared TEA within a few minutes.

The test is described in the Japanese documents JP-A-62 019 558 (Derwent Abstract No. 87-067647/10) and JP-A-62 005 939 (Derwent Abstract No. 87-047397/07), according to which the TEA is treated (neutralized) with acetic acid, citric acid, sulfuric acid, hydrochloric acid or phosphoric acid, and then the absorbance of the absorption bands at 420 nm and 530 nm is measured. If, during the test, the TEA does not develop any pink discoloration visible to the eye and if the measured values for the absorbance remain sufficiently low, then the TEA has a long shelf life as regards color, i.e. remains colorless over a period of several months.

The literature describes various processes for the preparation of pure and colorless to slightly colored TEA.

EP-A-4015 describes how ethanolamines with relatively low discoloration are prepared by adding phosphorous or hypophosphorous acid during or after the preparation of the ethanolamines.

EP-A-36 152 and EP-A-4015 illustrate the effect of the materials used in processes for the preparation of alkanolamines on the color quality of the process products and recommend nickel-free or low-nickel steels.

US-A-3 819 710 discloses a method of improving the color quality of ethanolamines by hydrogenating the crude ethanolamines in the presence of selected catalysts. The method is, however, technically complex and does not give TEA products which remain colorless over several months.

US-A-3 207 790 describes a method of improving the color quality of alkanolamines by adding a boron hydride of an alkali metal.

US-A-3 742 059 and DE-A-22 25 015 describe the improvement in the color quality of alkanolamines by adding an alkanolamine ester of boric acid or alkali metal/alkaline earth metal borates.

The presence of an auxiliary for stabilizing TEA is, however, undesirable in many important TEA application fields.

The subsequent addition of small amounts of ethylene oxide to freshly distilled TEA likewise leads, according to U.S. Pat. No. 4,673,762, to decoloration and color stability. However, the method appears hazardous for toxicological reasons.

GB-A-1 062 730 describes a method of purifying ethanolamines by carrying out the purification by distillation in the presence of silicates or aluminates.

JP-A-62 019 558 (Derwent Abstract No. 87-067647/10) reports on the preparation of high-quality TEA by treating crude TEA with inorganic oxides at from 170 to 250° C. and subsequently distilling the mixture in the absence of oxygen.

Similar results are achieved according to JP-A-62 005 939 (Derwent Abstract No. 87-047397/07) if crude TEA is heated with the exclusion of air for from 1 to 10 h at from 170 to 250° C., and then distilled under reduced pressure.

SU-A-326 178 (Derwent Abstract No. 63384T-AE) describes the preparation of TEA with good color quality by gently reacting anhydrous monoethanolamine (MEA) or diethanolamine (DEA) or mixtures of the two substances with ethylene oxide at temperatures less than 50° C.

Similar results are obtained according to SU-A-228 693 (Chem. Abstr. 70, 77305f (1969)) and GB-A-1 092 449 if ammonium is reacted with ethylene oxide at less than or equal to 35° C., and the resulting ethanolamine mixture is distilled with the exclusion of air.

For cost reasons, processes in which the reactions with ethylene oxide are carried out at low temperatures are unprofitable because of the long residence times and the low space-time yields associated therewith.

It is an object of the present invention to find an alternative, economic process for the preparation of pure, colorless (APHA color number less than or equal to 10) and color-stable triethanolamine (TEA) from aqueous ammonia and ethylene oxide.

We have found that this object is achieved by a method of purifying triethanolamine prepared by reacting aqueous ammonia with ethylene oxide in the liquid phase under superatmospheric pressure and at elevated temperature, which comprises removing excess ammonia, water and monoethanolamine (MEA) from the reaction product, reacting the resulting crude product with ethylene oxide at temperatures of from 110 to 180° C., and then rectifying the mixture in the presence of phosphorous or hypophosphorous acid or compounds thereof.

The method according to the invention can be carried out as follows:

Firstly, for example in accordance with GB-A-760 215 or EP-A-673 920, an ethanolamine mixture, comprising the main components monoethanolamine (MEA), diethanolamion [sic] (DEA) and triethanolamine (TEA), is prepared by reacting aqueous ammonia with ethylene oxide in the liquid phase under superatmospheric pressure and elevated temperature in a reactor provided with cooling. Preference is given here to the process as in EP-A-673 920.

The reaction temperatures here are generally from 110 to 160° C., preferably from 120 to 150° C., and the pressures are from 50 to 120 bar (5 to 12 MPa), preferably from 75 to 100 bar (7.5 to 10 MPa). The molar ratio of ammonia to ethylene oxide is from 1:1 to 100:1, preferably from 3:1 to 50:1, particularly preferably from 4:1 to 15:1, and the ammonia is used as a 60 to 99.99% strength, preferably 70 to 95% strength, aqueous solution. The ethylene oxide used can be added all at once or in from 2 to 10, preferably from 2 to 6, portions of in each case from 10 to 70% by weight (based on the total amount).

For example, the reaction of aqueous ammonia with ethylene oxide can be carried out in accordance with Example 15 on page 16 of GB-A-760 215 or, preferably, according to the two experiments No. 5 of Examples 1 and 2 in EP-A-673 920.

Then, in a manner known per se, the excess ammonia, together with some of the water, is distilled off from the resulting product under superatmospheric pressure, and then the remaining water is distilled off at reduced pressure.

This leaves a crude product comprising essentially MEA, DEA and TEA and having a water content of less than 0.3% by weight, preferably less than 0.1% by weight.

The monoethanolamine (MEA) is subsequently removed by distillation at reduced pressure to leave a crude product consisting of DEA, TEA and small amounts of secondary components, such as (2-(2-hydroxyethoxy)ethyl)di(2-hydroxyethyl)amine, (2-(2-hydroxyethoxy)ethyl)(2-hydroxyethyl)amine and N,N'-di(2-hydroxyethyl)piperazine. A typical content in this crude product of DEA is from about 75 to 80% by weight and of TEA is from about 25 to 20% by weight.

The composition of this crude product can vary depending on the molar ratio of ammonia to ethylene oxide originally used.

This crude product, which comprises DEA and TEA and has a water content of less than 0.3% by weight, preferably less than 0.1% by weight, and an ammonia content of less than 0.1% [sic] % by weight, preferably less than 0.01% by weight, is then reacted with from 0.6 to 1.2 mol, preferably from 0.8 to 1.1 mol, of ethylene oxide per gram-atom of nitrogen-bonded hydrogen in the crude product at temperatures of from 110 to 180° C., preferably from 120° C. to 180° C., in the liquid phase. This reaction is generally carried out as described in GB-A-1 453 762. The reaction is preferably carried out in tubular reactors and in a plurality of stages, from 50 to 80% by weight of the ethylene oxide used, for example, being reacted in a first reaction stage at temperatures of preferably from 125 to 165° C., the remaining amount of ethylene oxide used being reacted in a second reaction stage at temperatures of preferably from 150 to 180° C., and the reaction being concluded in a third reaction stage at temperatures of from 120 to 150° C.

The reaction of the crude product comprising DEA and TEA with ethylene oxide can, for example, be carried out at as described in Example 12 on page 4 of GB-A-1 453 762.

This gives a TEA crude product with a content of about 80% by weight of TEA and about 20% by weight of DEA, and secondary components, for example of the type described above, in small amounts.

Finally, in accordance with EP-A-4015, an effective amount of phosphorous or hypophosphorous acid ($H_3PO_3$ or $H_3PO_2$) or compounds thereof, preferably phosphorous acid, is added to the resulting TEA crude product, and the mixture is rectified under reduced pressure.

The phosphorous or hypophosphorous acid can be added in monomeric or, where appropriate, polymeric form, in hydrous form (hydrates), as addition compound, or salt, such as disodium hydrogenphosphite $Na_2HPO_3$. Compounds of phosphorous or hypophosphorous acid, such as esters, are also suitable.

The amount of phosphorus compounds added is usually at least 0.01% by weight, preferably from 0.01 to 2% by weight, particularly preferably from 0.02 to 1.0% by weight, very particularly preferably from 0.02 to 0.1% by weight, based on the amount of crude TEA used; the effect does, however, also occur with larger amounts.

The rectification is preferably carried out continuously and at a pressure of less than 10 mbar (10 hPa), for example from about 1 to 2 mbar, low-boiling fractions being withdrawn overhead. This gives a pure TEA in the sidestream takeoff.

The method according to the invention gives a triethanolamine (TEA) with a purity of greater than 99%, preferably greater than 99.4%, which, directly after rectification, has an APHA color number of from 0 to 10, in particular from 0 to less than 6, very particularly from 0 to 5, and even after a storage time of at least 6 months in a sealed pack with the exclusion of light at temperatures of from 10 to 30° C., has an APHA color number of less than 50, in particular of less than 40, very particularly of less than 35.

The product of the method according to the invention does not show a pink discoloration in the "acid neutralization test" mentioned at the outset either directly following rectification or after a storage time of at least 6 months (storage conditions as above).

The process product according to the invention has, after an acid treatment, which is carried out as described at the end of the example within from about 0.5 to 1 hour after the product has been obtained, a value for the numerical measure a* according to the CIE Lab system of less than or equal to 10, in particular of less than 7, very particularly of less than 3.

EXAMPLE 1

2300 kg of a DEA/TEA crude mixture (content: from about 75 to 80% by weight of DEA and from about 25 to 20% by weight of TEA), which had been obtained by distillative removal of the MEA fraction at from 30 to 100 mbar from a crude mixture of the ethanolamines MEA, DEA and TEA, prepared as in No. 5 of Examples 1 and 2 in EP-A-673 920 from aqueous ammonia and ethylene oxide under superatmospheric pressure, were reacted further in a 1st stage with 330 kg of ethylene oxide in a tubular reactor (20 $m^2$ internal area) at about 145° C. in an exothermic reaction, and then in a 2nd stage likewise in a tubular reactor (3.8 $m^2$ internal area) with a further 165 kg of ethylene oxide at about 165° C.

In a further tubular reactor (3.8 $m^2$ internal area), the 3rd reaction stage, the reaction was concluded, the reaction mixture was cooled to about 140° C. and conveyed directly into the receiver of a subsequent continuous, fractionating rectification, or alternatively cooled further to 80° C., stored temporarily and then passed to the continuous rectification only via the described distillation receiver.

1600 kg of crude TEA obtained in this way (composition: about 80% by weight of TEA, about 20% by weight of DEA and less than about 1% by weight of secondary components such as, for example, (2-(2-hydroxyethoxy)ethyl)di(2-hydroxyethyl)amine were, after about 0.56 kg of phosphorous acid ($H_3PO_3$) (0.035% by weight calculated on the amount of crude TEA used) had been metered in, preheated to about 150 to 180° C. [lacuna] conveyed to a continuous-operation rectification column.

The rectification column was fitted with a circulation evaporator.

At a reduced pressure of 2 mbar (2 hPa), about 500 kg of low-boiling fractions (content: about 70% by weight of DEA and about 30% by weight of TEA) were removed via the head of the column.

About 900 kg of colorless, pure TEA (color number: 0–5 APHA) with a content of 99.5 to 99.7% (GC) were obtained via the sidestream takeoff of the column.

About 200 kg of residue (composition: from about 90 to 95% by weight of TEA; remainder: high boilers, such as, for example, (2-(2-hydroxyethoxy)ethyl)di(2-hydroxyethyl) amine, were removed from the bottom of the column via a downstream thin-film evaporator at a reduced pressure of from about 1.5 to 2 mbar (1.5 to 2 hPa). The top distillate of the thin-film evaporator was returned to the still of the TEA rectification column.

The TEA prepared in this manner had a color number of 30 APHA after a storage time of 6 months in a sealed pack with the exclusion of light at temperatures of from 10 to 30° C., minimal discoloration which was just detectable by the eye as a pale yellow coloration.

The APHA color numbers were measured in accordance with DIN-ISO 6271.

The TEA prepared in this manner did not obviously turn pink following acid treatment, which was carried out as described below, nor after acid treatment was carried out after the TEA had been stored for 6 months under the abovementioned conditions. ("Acid neutralization test").

The TEA prepared in this way had, after an acid treatment, which was carried out as described below within from 0.5 to 1 hour after the product had been obtained, a value for the numerical measure a* according to the CIE Lab system of less than 3.

To assess the color quality of the prepared TEA, the latter was firstly treated with an acid as described below and the numerical measure a* was determined according to the CIE Lab system:

35 g of a sample of pure TEA, 7.5 g of 1,2-propanediol and 6.0 g of 85% strength phosphoric acid were thoroughly mixed by stirring and heated to 100° C. for 20 min in a heating cabinet. The numerical measures L*, a* and b* of the CIE Lab system according to Judd and Hunter (CIE= Comission International d'Eclairage, Paris) were then determined for this TEA sample treated in this way in a spectral color measurement in a LICO 200 device from the company Dr. Lange using a 5 cm cuvette.

The numerical measure a* here describes the amount of red in the sample.

Comparative Example 2300 kg of a DEA/TEA crude mixture (content: from about 75 to 80% by weight of DEA and from about 25 to 20% by weight of TEA), which had been obtained as described in the above example from aqueous ammonia and ethylene oxide, were, following removal of MEA, subjected to continuous fractional rectification at from 10 to 15 mbar with removal of most of the DEA.

1700 kg of crude TEA obtained in this way (composition: about 80% by weight of TEA, about 20% by weight of DEA and less than about 1% by weight of secondary components, such as, for example, (2-(2-hydroxyethoxy)ethyl)di(2-hydroxyethyl)amine were, after about 0.6 kg of phosphorous acid ($H_3PO_3$) (0.035% by weight calculated on the amount of crude TEA used) had been metered in, preheated to about 150 to 180° C. and conveyed to the receiver of a continuous-operation rectification column.

The rectification column was fitted with a circulation evaporator.

At a reduced pressure of 2 mbar (2 hPa), about 600 kg of low-boiling fractions (content: about 70% by weight of DEA and about 30% by weight of TEA) were removed via the head of the column.

About 900 kg of colorless, pure TEA (color number: 3 APHA) with a content of 99.5 to 99.7% (GC) were obtained via the sidestream takeoff of the column.

About 200 kg of residue (composition: about 90–95% by weight of TEA; remainder: high boilers, such as, for example, (2-(2-hydroxyethoxy)ethyl)di(2-hydroxyethyl) amine, were removed from the bottom of the column via a downstream thin-film evaporator at a reduced pressure of from about 1.5 to 2 mbar (1.5 to 2 hPa). The top distillate of the thin-film evaporator was returned to the still of the TEA rectification column.

The TEA prepared in this way had a color number of greater than 50 APHA, which was observed as a clear yellow coloration, after a storage time of 6 months in a sealed pack with the exclusion of light at from 10 to 30° C.

The TEA prepared in this way had, after an acid treatment, which was carried out as described above within from 0.5 to 1 hour after the product had been obtained, a value for the numerical measure a* according to the CIE Lab system of greater than 10.

EXAMPLE 2

2300 kg of a DEA/TEA crude mixture (content: from about 75 to 80% by weight of DEA and from about 25 to 20% by weight of TEA), which had been obtained as described in Example 1, were further reacted in a 1st stage with 435 kg of ethylene oxide in a tubular reactor (20 m² internal area) at about 150° C. in an exothermic reaction, and then in a 2nd stage, likewise in a tubular reactor (3.8 m² internal area), with a further 220 kg of ethylene oxide at about 170° C.

The remaining procedure was as described in Example 1.

The TEA prepared in this manner did not obviously turn pink following acid treatment, which was carried out as described in Example 1, nor after the acid treatment was carried out after the TEA had been stored for 6 months under the conditions stated in Example 1 ("acid neutralization test").

The TEA prepared in this way had, after an acid treatment, which was carried out as described in Example 1 and within from 0.5 to 1 hour after the product had been obtained, a value for the numerical measure a* according to the CIE Lab system of less than 3.

EXAMPLE 3

2300 kg of a DEA/TEA crude mixture (content: from about 75 to 80% by weight of DEA and from about 25 to 20% by weight of TEA), which had been obtained as described in Example 1, were reacted with the total amount of 495 kg of ethylene oxide according to Example 1 in a single stage (tubular reactor 20 m² internal area) at 160° C., passed through the 2nd tubular reactor (3.8 m² internal area) and finished off in the 3rd tubular reactor (3.8 m² internal area).

The remaining work-up was carried out as in Example 1.

The TEA prepared in this way had the same properties as given in Example 1.

EXAMPLE 4

2300 kg of a DEA/TEA crude mixture, corresponding to Example 1, were used, but the addition of 330 kg of ethylene oxide took place in the 1st stage at about 160° C. and the remaining 165 kg of ethylene oxide in the 2nd stage at about 180° C.

The TEA prepared in this way had the same properties as given in Example 1.

EXAMPLE 5

1600 kg of crude TEA prepared by further ethoxylation of the DEA/TEA crude mixture according to Example 1 (composition: about 80% by weight of TEA, about 20% by weight of DEA and less than about 1% by weight of secondary components, such as, for example, 2-(2-hydroxyethoxy)ethyl di(2-hydroxyethyl)amine), were, after the metered addition of about 4.8 kg of phosphorus acid ($H_3PO_3$) (0.3% by weight based on the amount of crude TEA used), conveyed, preheated to about from 150 to 180° C., to a continuously operated rectification column.

The remaining procedure corresponded to that of Example 1.

The TEA prepared in this manner had the same properties as for the preparation according to Example 1.

We claim:

1. A method of purifying triethanolamine prepared by reacting aqueous ammonia with ethylene oxide in the liquid phase under pressure and at elevated temperature, which comprises removing excess ammonia, water and monoethanolamine from the reaction product, reacting the resulting crude product with ethylene oxide at temperatures of from 110 to 180° C., and then rectifying the mixture in the presence of phosphorous or hypophosphorous acid or compounds thereof.

2. A method as claimed in claim 1, wherein the crude product resulting following removal of excess ammonia, water and monoethanolamine is reacted with from 0.6 to 1.2 mol of ethylene oxide per gram-atom of nitrogen-bonded hydrogen in the crude product.

3. A method as claimed in claim 1, wherein, following removal of excess ammonia, water and monoethanolamine, the reaction with ethylene oxide is carried out in a plurality of stages.

4. A method as claimed in claim 1, wherein the mixture is rectified in the presence of at least 0.01% by weight, based on the amount of crude triethanolamine, of phosphorous or hypophosphorous acid or compounds thereof.

5. A method as claimed in claim 1, wherein the rectification is carried out in the presence of phosphorous acid.

6. A method as claimed in claim 1, wherein the purified triethanolamine has, after acid treatment, a value for the numerical measure a* according to the CIE Lab system of less than or equal to 3.

7. A method as claimed in claim 1, wherein the APHA color number (DIN-ISO 6271) of the purified triethanolamine during storage for 6 months in a sealed pack with the exclusion of light at temperatures of from 10 to 30° C. is less than 50.

8. A method as claimed in claim 7, wherein the APHA color number of the purified triethanolamine during storage for 6 months in a sealed pack with the exclusion of light at temperatures of from 10 to 30° C. is less than 35.

* * * * *